United States Patent [19]
Jinotti

[11] Patent Number: 5,487,381
[45] Date of Patent: Jan. 30, 1996

[54] CLOSED SYSTEM FOR TREATING PULMONARY PATIENT

[76] Inventor: Walter J. Jinotti, 10 Scott St., New Brunswick, N.J. 08903

[21] Appl. No.: 230,507

[22] Filed: Apr. 20, 1994

[51] Int. Cl.⁶ ................................................. A61M 16/20
[52] U.S. Cl. ............................. 128/207.14; 128/207.16
[58] Field of Search ......................... 128/207.14, 207.15, 128/207.16, 207.17

[56] References Cited

U.S. PATENT DOCUMENTS

| | | | |
|---|---|---|---|
| 746,794 | 3/1956 | Davis | 128/207.16 |
| 4,502,482 | 3/1985 | DeLuccia et al. | 128/207.15 |
| 5,133,345 | 7/1992 | Lambert | 128/207.14 |
| 5,140,983 | 8/1992 | Jinotti | 128/207.14 |
| 5,277,177 | 1/1994 | Page et al. | 128/207.14 |
| 5,329,921 | 7/1994 | Socaris et al. | 128/207.16 |
| 5,354,267 | 10/1994 | Niermann et al. | 128/207.14 |

*Primary Examiner*—Edgar S. Burr
*Assistant Examiner*—V. Srivastava
*Attorney, Agent, or Firm*—Robert A. Green

[57] ABSTRACT

The apparatus comprises a T-shaped member adapted to be inserted into the mouth of a patient and feeding oxygen thereto. The T-shaped member is divided into front and rear portions by an apertured wall into which a catheter assembly is to be inserted for insertion into a patient. The aperture in the wall is controlled by a rotary rod or valve having a through-hole which can be aligned with the aperture in the wall in one position and which is out of alignment with the wall in another position.

10 Claims, 2 Drawing Sheets

CLOSED SYSTEM FOR TREATING PULMONARY PATIENT

BACKGROUND OF THE INVENTION

Apparatus for treating a pulmonary patient by way of an endotracheal tube inserted through the patient's mouth is disclosed and claimed in U.S. Pat. No. 5,140,983 of the present inventor. This patent and others set forth below are incorporated herein by reference. The apparatus described in U.S. Pat. No. 5,140,983 operates satisfactorily but it does not lend itself to mass production by a molding operation.

SUMMARY OF THE INVENTION

The above-described problem is solved in accordance with the present invention. Apparatus embodying the invention includes a T-shaped plastic device having a first tube for insertion into the patient's mouth, a second tube communicating with the first tube for coupling oxygen thereto and to the patient. A third tube is coupled to the first tube but is separated therefrom by a wall having an aperture.

A catheter assembly is adapted to be inserted through the third tube and the aperture in the separating wall and through the first tube into the patient. A rotary valve assembly is provided adjacent to the apertured wall and in one rotary position, it permits access to the aperture in the wall so that the catheter can pass through and in anaother rotary position, when the catheter is removed, it blocks the aperture in the wall. The assembly can be readily molded and provides a liquid-tight structure in front of the apertured wall.

DESCRIPTION OF THE INVENTION

Figure 1:
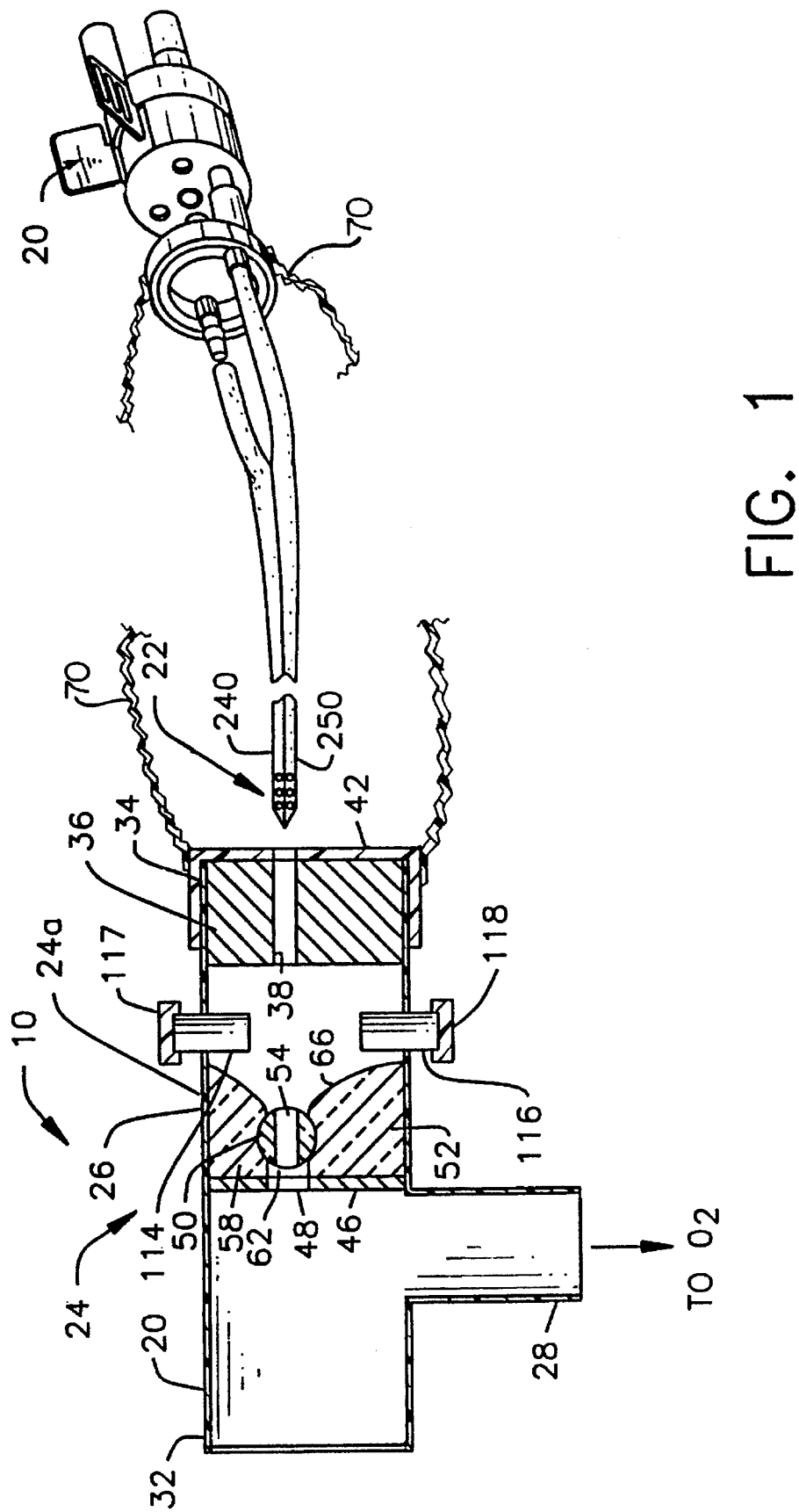
FIG. 1 is a side elevational view, partly in section, of apparatus embodying the invention.

Pulmonary apparatus 10 embodying the invention, referring to FIG. 1, includes a dual-purpose catheter assembly of the type disclosed and claimed in U. S. Pat. No. 4,595,005 which is incorporated herein by reference. This catheter assembly includes a double lumen unit 22, having flexible plastic tubes or lumens 240 and 250 suitably secured together, tube 240 being used to supply oxygen and tube 250 being used for applying suction to a patient.

The tubes 240 and 250 are coupled to the patient end of a valve 20 which is operated by a nurse to control the application of oxygen or suction coupled from sources thereof to the supply side of the valve 20. The valve 20 is preferably of the type known as a blocking valve which is described and claimed in U.S. Pat. Nos. 5,140,983 and 5,088,486 which is also incorporated herein by reference.

It is to be understood that other catheter assemblies may be used in practicing the present invention.

The apparatus 10 includes a T-shaped connector 24 by means of which the patient can be connected to endotracheal apparatus not described herein. The T-shaped connector 24 is preferably of plastic and includes a generally tubular cross member 26 shown oriented horizontally in FIG. 1 which represents the crossbar of the "T" and has a front end or patient end 32 which is adapted to be place in a patient's mouth. The other end or rear end 34 of the cross member may carry within it a cleaning sponge or the like 36 as shown in U.S. Pat. No. 5,140,983. The sponge has a through-hole 38 through which the catheter assembly 22 can pass when it is to be inserted into a patient for treatment.

A removable cap 42 rear wall is secured, in friction tight engagement, to the rear end of the connector 24 and it is removed to permit the sponge 36 to be removed and replaced.

The T-shaped connector 24 also includes an auxiliary tubular member 28 which extends downwardly from the crossbar 26 and this member is adapted to be connected to a source of oxygen to be introduced in the patient.

A transverse wall 46 having a hole 48, through which the catheter assembly 22 can pass, is provided in the crossbar 26 rearwardly of the depending tubular member 28 and, in effect, divides the crossbar 26 into a front portion and a rear portion 24A.

Means is provided in the rear portion 24A of the crossbar 26 to permit lavage thereof. This means comprises a first short tube 114 disposed within the wall of the crossbar, from above, and disposed vertically along the vertical axis thereof. The tube 114 extends a suitable distance into the portion 24A. A second similar tube 116 is disposed at the lower end of the vertical axis of the crossbar and extends from the inside of portion 24A to the exterior thereof. The outer end of tube 114 has a removable cap 117 and the outer end of tube 116 has a removable cap 118. The tubes 114 and 116 may be of plastic or any other suitable material.

As described in U.S. Pat. No. 5,140,983, the tube 114 can be connected to suction to clean out the portion 24A with tube 116 open as a vent. Tube 116 can also be held open as a vent when oxygen is fed into the valve 20 from the oxygen source but is not applied to the patient. Fluid can also be introduced into tube 114 for cleaning purposes.

In order to provide controlled access of the catheter 22 from the rear chamber 24dA through the wall 46 to the patient, a rotatable rod or valve 50 is mounted horizontally and transverse to the long axis of connectgor 24 within rear portion 24A. The rod 50 is rotatably positioned in a glass or plastic body 52 disposed within portion 24A and having its rear wall 58 which bears against the rear surface of wall 46. The glass body 52 has a through hole 62 aligned with hole 48 in wall 46. The front wall 66 of body 52 is flared to provide a funnel structure to guide the catheter assembly.

The rod 50 includes a through-hole 54 of a diameter such that the catheter assembly 22 can pass therethrough. The glass body 52 and rod 50 are similar in structure and function to a petcock used in laboratory equipment.

Figure 2:
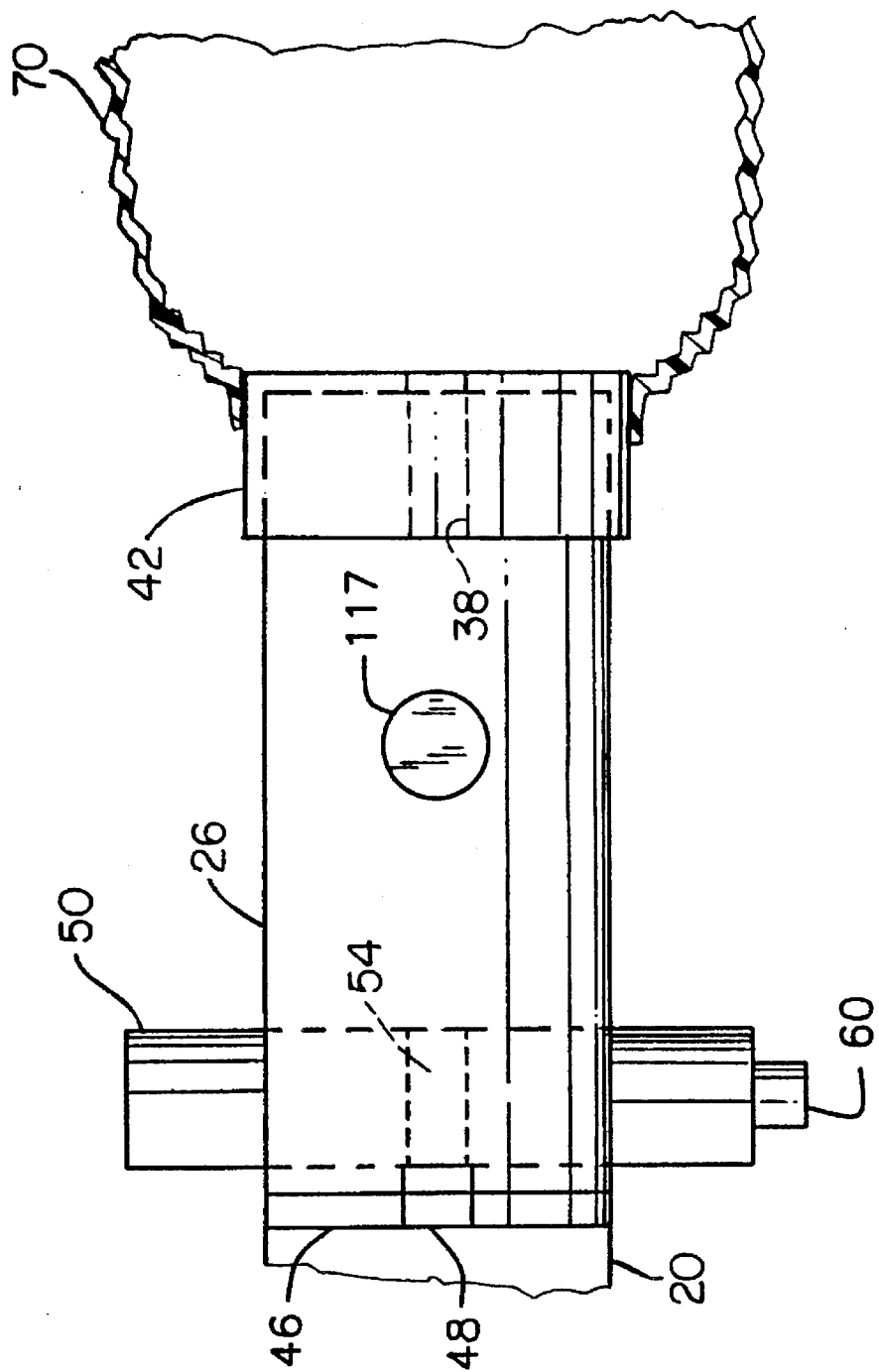
FIG. 2 is a plan view of a portion of the apparatus of FIG. 1.

The rod 50, as seen in FIG. 2, is disposed on a horizontal axis transverse to the long axis of the cross bar and extends through the two opposed walls of the crossbar in water-tight engagement therewith and externally thereof, one end of the rod has a suitable enlargement 60 by which an operator can rotate the rod.

When the rod 50 is disposed with its through-hole 54 aligned with the aperture 48 in the wall 46, the catheter assembly can be pushed through, guided by the funnel-like front wall 66 of the body 52, and inserted into the mouth of a patient to provide suction or oxygen thereto by operation of the valve 20. After the catheter assembly is withdrawn into the rear chamber 24A, the rod 50 is rotated so that its through-hole 54 is out of alignment with the aperture 48 in wall 46 and the two lumens are cleaned on the sponge 36.

In addition, cleaning liquid or the like can be introduced through tube 114 without the fluid leaking out of the chamber 24A.

As shown in U.S. Pat. No. 5,140,983 a sleeve 70 encloses the catheter assembly and is coupled between the removable cap 42 and the valve 20. The sleeve is detachable connected so that it can be removed and thrown away if desired and similarly, the catheter assembly 22 can be thrown away after each use if desired.

It is to be understood that the rod 50 may take other shapes within the spirit of the invention. For example it may be a ball having a handle, like handle 60 by which it can be rotated.

It has been found that the valve 20 is not completely air tight and that when suction is applied a small amount of leakage of air occurs and this increases dramatically the speed and efficiency of the valve in removing mucus from a patient. It appears that a Venturi-type action occurs in the valve.

What is claimed is:

1. Medical apparatus comprising a closed system for providing oxygen and suction to a patient including a tubular member having a front patient portion and a rear portion, said rear portion having a front end and a rear end, a first wall disposed between said front patient portion and said front end of said rear portion, said first wall having a front surface and a rear surface, a hole in said first wall, a second wall at said rear end of said rear portion closing off said rear portion of said tubular member, said second wall having means for permitting a catheter to enter and leave said tubular member, an auxiliary tubular member coupled to said front patient portion for providing treatment means to a patient, a valve member comprising a rod having a through-hole rotatably mounted in said rear portion of said tubular member closely adjacent to said rear surface of said first wall and in fluid tight engagement therewith, a through-hole in said valve member, said through-hole being aligned with said hole in said first wall in one position of said valve member to permit a catheter to pass through and said through-hole being out of alignment with said hole in said first wall in another position of said valve member, said valve member providing a leakproof block of said hole in said wall when said valve member is in said another position, means coupled to said second wall of said rear portion of said tubular member for inserting a catheter therein and into said tubular member and for removing a catheter after it has been withdrawn from a patient through said front portion of said tubular member, and means coupled to said rear portion of said tubular member for admitting a washing fluid into said rear portion and for washing a catheter after it has been withdrawn from a patient, said first wall and said valve member and said second wall forming a relatively fluid tight washing chamber for said tubular member.

2. The apparatus defined in claim 1 wherein said valve member is embedded in an insulating body which forms a fluid tight seal with the rear surface of said first wall.

3. The apparatus defined in claim 1 and including flexible tube means slidably coupled to said rear portion and insertable through said second wall and said rear portion and said front portion of said tubular member into a patient, and a control valve coupled to said flexible tube means for admitting oxygen and suction into said tubular member and a patient.

4. The apparatus defined in claim 3 and including a protective sleeve enclosing said flexible tube means and extending from said control valve to said rear end of said second portion of said tubular member.

5. The apparatus defined in claim 1 and including a sponge in said rear portion.

6. The apparatus defined in claim 1 and including a removable cap in friction tight engagement with the rear end of said rear portion.

7. The apparatus defined in claim 1 and including a catheter assembly inserted into said rear portion and through said valve and said first wall and into a patient to provide suction and oxygen thereto, said catheter assembly being removed and discarded from said rear portion after a patient has been treated.

8. The apparatus defined in claim 1 and including a cap secured to said rear end of said rear portion of said tubular member.

9. The apparatus defined in claim 1 wherein said tubular member is generally T-shaped with said front and rear portions being aligned with each other and said auxiliary tubular portion extends at an angle to said front rear portions.

10. A closed system for treating a patient with suction and oxygen and other medication comprising a T-shaped tubular member having a front patient portion and a rear portion for supplying oxygen and suction and medication to a patient, a wall having an aperture separating said front patient portion from said rear portion of said tubular member, means providing a generally leak-proof washing chamber in said rear end of said tubular member in leak-proof contact with said apertured wall, said means including a rotatable valve comprising a rod having a through-hole which, in one position of said valve is in alignment with said hole in said wall and permits communication between said front patient portion and said rear portion of said tubular member, and in another position of said valve, is out of alignment with said hole in said wall whereby said front patient portion is blocked from said rear portion and means coupled to said rear portion of said tubular member providing a controlled supply of oxygen, suction and medication to said T-shaped member and a patient.

\* \* \* \* \*